United States Patent
Findlay et al.

(10) Patent No.: US 10,175,156 B2
(45) Date of Patent: Jan. 8, 2019

(54) PRESSURE TEST CELL

(71) Applicant: Score Group PLC, Peterhead (GB)

(72) Inventors: Brian Fraser Findlay, Peterhead (GB); Ian McGregor Cheyne, Inverkeithing (GB); Ian Andrew Jamieson, Blackridge (GB)

(73) Assignee: Score Group PLC, Peterhead (GB)

( * ) Notice: Subject to any disclaimer, the term of this patent is extended or adjusted under 35 U.S.C. 154(b) by 28 days.

(21) Appl. No.: 15/114,168

(22) PCT Filed: Jan. 12, 2015

(86) PCT No.: PCT/GB2015/050045
§ 371 (c)(1),
(2) Date: Jul. 26, 2016

(87) PCT Pub. No.: WO2015/118293
PCT Pub. Date: Aug. 13, 2015

(65) Prior Publication Data
US 2017/0205324 A1    Jul. 20, 2017

(30) Foreign Application Priority Data

Feb. 5, 2014 (GB) .................................. 1401989.7

(51) Int. Cl.
| | |
|---|---|
| *G01N 3/12* | (2006.01) |
| *E04H 5/04* | (2006.01) |
| *E04B 1/98* | (2006.01) |
| *F42D 5/045* | (2006.01) |

(Continued)

(52) U.S. Cl.
CPC ................. *G01N 3/12* (2013.01); *E04B 1/92* (2013.01); *E04B 1/98* (2013.01); *E04H 1/005* (2013.01);

(Continued)

(58) Field of Classification Search
CPC .. G01N 3/12; E04B 1/92; E04H 1/005; E04H 5/02; E04H 7/04; E04H 9/10; E06B 5/12; F42D 5/045
See application file for complete search history.

(56) References Cited

U.S. PATENT DOCUMENTS

| 4,577,487 A * | 3/1986 | Dooley | ................ G01N 29/227 |
| | | | 73/37 |
| 2004/0057043 A1* | 3/2004 | Newman | ................ G01M 3/363 |
| | | | 356/237.1 |

(Continued)

FOREIGN PATENT DOCUMENTS

| CH | 573035 A5 | 2/1976 |
| CN | 102913008 A | 2/2013 |

(Continued)

OTHER PUBLICATIONS

Decker, Robert, "International Search Report," as prepared for PCT/GB2015/050045, dated Mar. 23, 2015, three pages.

Primary Examiner — Hezron E Williams
Assistant Examiner — David Z Huang
(74) Attorney, Agent, or Firm — Winstead PC

(57) ABSTRACT

A test cell (10) for containing equipment (12) subject to pressure testing comprises a plurality of metal plate wall panels (14) and a mesh roof panel (16) formed from mesh strands (26) of a high strength material. Each wall panel has a lapped connection (18) with an adjacent wall panel. The mesh panel (16) may be formed from a ballistic fabric, and the mesh strands (26) may be wire, rope and braid of steel, metal, plastic, natural or composite fiber, or a combination thereof. In the event of a pressure failure of the equipment (12) under test, the roof panel (16) captures fragments of the equipment while allowing the dissipation of pressure shock waves through the apertures (28) in the mesh. The lapped connections (18) between wall panels (14) result in (Continued)

increased friction between adjacent wall panels (14) and thus an increase in the strength of the connection when subject to pressure shock waves.

18 Claims, 3 Drawing Sheets

(51) Int. Cl.
*E04B 1/92* (2006.01)
*E04H 1/00* (2006.01)
*E04H 5/02* (2006.01)
*E04H 7/04* (2006.01)
*E04H 9/10* (2006.01)
*E06B 5/12* (2006.01)

(52) U.S. Cl.
CPC ............... *E04H 5/02* (2013.01); *E04H 5/04* (2013.01); *E04H 7/04* (2013.01); *E04H 9/10* (2013.01); *E06B 5/12* (2013.01); *F42D 5/045* (2013.01)

(56) References Cited

U.S. PATENT DOCUMENTS

| 2005/0223651 | A1* | 10/2005 | Lange-Kornbak | E04H 9/10 52/45 |
| 2006/0112532 | A1* | 6/2006 | Rexroad | A62B 1/22 29/433 |
| 2010/0162929 | A1* | 7/2010 | Smit | E04B 1/3483 109/79 |
| 2015/0020463 | A1* | 1/2015 | Toubia | E04B 1/34321 52/79.9 |

FOREIGN PATENT DOCUMENTS

| DE | 202009010570 U1 | 10/2009 |
| EP | 1580340 A2 | 9/2005 |
| EP | 2273021 A1 | 1/2011 |
| GB | 2499564 A | 8/2013 |
| WO | WO-2007112147 A2 | 10/2007 |

* cited by examiner

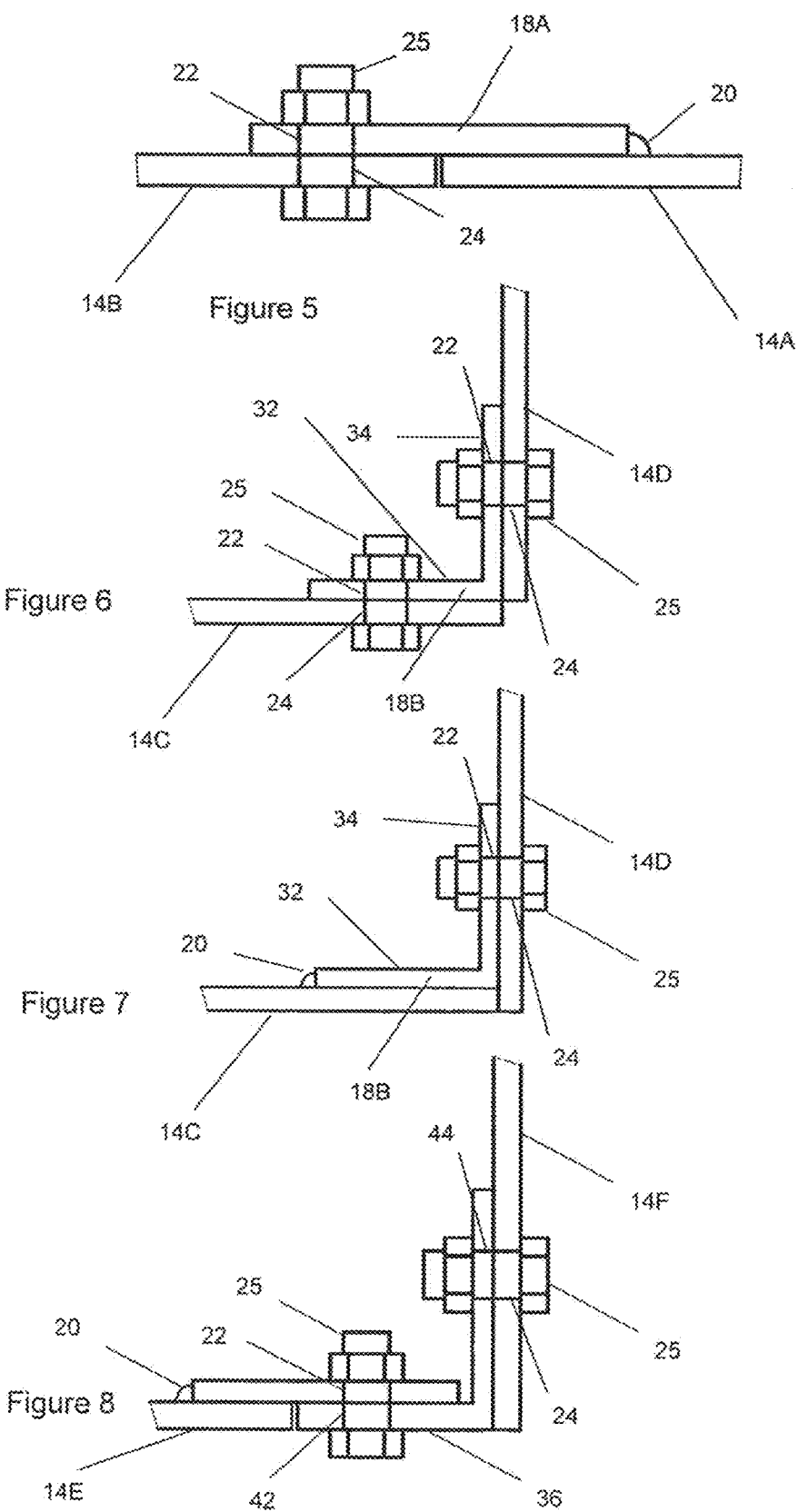

PRESSURE TEST CELL

FIELD OF THE INVENTION

The invention relates to a test cell for containing equipment subject to pressure testing, in particular a test cell for carrying out a safe method of pressure testing in an enclosed testing environment. The invention also relates to a test cell system for the construction of such test cells.

BACKGROUND OF THE INVENTION

Pressure testing is used to test equipment and components across a range of industries. One example of this is the oil industry, where there is a need to test valves under a controlled pressure before they are shipped for use. New and refurbished valves are typically tested to a test pressure of 150% of their expected operating conditions to ensure that they can safely contain their contents. Such testing can result in failure of a valve. If this happens the valve could explode, resulting in fragments emanating from the failure becoming projectiles and injuring those in the area of the test. It is therefore desirable to carry out such testing in a safe enclosure, referred to herein as a test cell.

Traditionally pressure testing has been conducted either in a large open space or in various types of enclosures, constructed of brick, concrete, or ballistic Perspex™. Research has shown that these structures do not offer adequate protection to those immediately adjacent to, or in close proximity to, the enclosure in the event of a failure of an item under test where the pressurised volume in the item under test is large and the applied pressure at failure is high. Research has shown that fragments generated in such a failure can directly penetrate these existing enclosures, or can cause the creation of fragments from outside of the enclosure due to scabbing. Scabbing is of particular concern in concrete structures as it is caused by the reflection of the compressive blast wave from the outside face of the enclosure as a tensile wave. This results in an impulsive generation of a piece of fast moving concrete that is detached from the main wall of the enclosure due to material failure of the concrete under tension.

Tests have shown that in order to reduce this risk to an acceptable level during pressure testing of a large high pressure valve (for example a 36" (914 mm) diameter class 2500 valve), a concrete enclosure would require walls more than 4.5 m thick.

Another disadvantage of prior art test cells is their method for dissipating quasi static pressure. When a vessel under pressure fails, the resulting pressure wave can reflect off the walls of the enclosure of the test cell, resulting in a pressure wave with a greater impulse due to the addition of incident and reflected pressure pulses. The pressure due to this increased pressure wave is referred to as the quasi static pressure. The quasi static pressure can have enough impulse to cause a failure in the enclosure. Most current enclosures dissipate this pressure either by leaving the roof of the enclosure exposed or by having a blast roof which lifts or is frangible to dissipate and/or absorb the pressure. This has the disadvantage that portions of the roof may then themselves become projectiles, causing a hazard to those persons in the vicinity.

It is an object of the present invention to overcome one or more of the disadvantages of the prior art.

DISCLOSURE OF THE INVENTION

According to a first aspect of the present invention, there is provided a test cell for containing equipment subject to pressure testing, the test cell comprising:

a plurality of wall panels, each wall panel having a lapped connection with an adjacent wall panel, a roof panel fixedly connected to the plurality of wall panels, wherein each wall panel comprises a metal plate, and wherein the roof panel comprises a mesh panel formed from mesh strands of a high strength material.

Each lapped connection may comprise a lapping plate fixed to one vertical edge of the corresponding wall panel and provided with apertures for fixing with bolts to corresponding apertures provided at an adjacent vertical edge of an adjacent wall panel.

The roof panel is capable of capturing fragments of the equipment under test, in the case of a pressure failure of the equipment. The roof panel allows for the dissipation of the quasi static pressure arising from a pressure failure of the equipment through apertures in the mesh panel, while the roof panel still remains intact.

Preferably the metal plate is a steel plate. Using walls of steel instead of concrete or brick drastically reduces the space and wall thickness required for safely testing high volume items at high pressure.

In one or more of the plurality of wall panels, the lapping plate may extend in a plane parallel to the plane of the wall panel. Such a lapping plate is adapted to be fixed to an adjacent wall panel coplanar with the wall panel to which the lapping plate is permanently fixed, for example to form a continuous planar wall of the test cell.

In one or more of the plurality of wall panels, the lapping plate may extend in a plane perpendicular to the plane of the wall panel. Such a lapping plate is adapted to be fixed to an adjacent wall panel perpendicular to the wall panel to which the lapping plate is permanently fixed, for example to form a corner of the test cell.

The mesh strands are selected from wire, rope and braid of steel, metal, plastic, natural or composite fibre, or a combination thereof.

The mesh panel may be of plastic or composite material and may be extruded, oriented, expanded, woven or tubular. It can be made from polypropylene, polyethylene, nylon, PVC, PTFE, natural fibres, polyamides, ultra high molecular weight polyethylene (UHMWPE), or proprietary fabrics such as Dyneema™, Kevlar™ and Nomex™.

The mesh panel may be of metal and may be woven, knitted, welded, expanded, photo-chemically etched or electroformed from steel or other metals.

The mesh panel may comprise a ballistic fabric.

Preferably the mesh panel has an aperture size which permits a camera positioned above the mesh panel to record optical images of the equipment under test below the mesh panel.

The mesh panel may have apertures having an aperture size such that the width of each aperture is at least 5 mm, or at least 25 mm.

The apertures may make up at least 25% of the area of the mesh panel, and optionally at least 50% of the area of the mesh panel.

Preferably the mesh panel blocks passage of fragments having a size of more than 5 mm or more than 25 mm or more than 50 mm.

The roof panel may be connected to the plurality of wall panels by mesh connecting means comprising a plurality of hooks arranged at or near an upper horizontal edge of each of the plurality of wall panels.

The test cell may further comprise testing equipment for monitoring the equipment subject to pressure testing, the testing equipment being selected from one or more of pressure monitoring equipment, pressurised air delivery equipment, thermal sensing equipment, and pressurised water delivery equipment.

The test cell may further comprise a camera fixed to one of said wall panels and arranged above the roof of the test cell to provide a view of the interior of the test cell through the roof.

The test cell may further comprise a floor, wherein each wall panel is fixed to the floor. The floor may be a steel floor.

The test cell may further comprise a tank adapted to hold liquid, and a lifting means adapted to lower the equipment subject to pressure testing into the tank and to raise the equipment subject to pressure testing from the tank. The tank may comprise a pit in the floor.

The test cell may further comprise a plurality of wall corner members, each wall corner member being adapted for connection with one or more of said wall panels.

One or more of the wall panels may include a door. In a particular embodiment one or more of the wall panels may comprise a door mounting panel, comprising a wall section and a door hingedly fixed to the wall section.

Each wall panel may comprise floor fixing means adapted to fix the wall panel to the floor. The floor fixing means may comprise an angle member having a web and a flange, wherein the web is fixed to the wall panel and the flange member is adapted to be fixed to the floor.

According to a second aspect of the present invention, there is provided a modular test cell system for the construction of test cells for containing equipment subject to pressure testing, the test cell system comprising:

a plurality of wall panels, each of said wall panels having substantially the same size, a plurality of roof panels adapted for connection to said plurality of wall panels, each of said roof panels having a different size, wherein each wall panel comprises a metal plate, wherein each roof panel comprises a mesh panel formed from mesh strands of a high strength material, and wherein each roof panel of different size is adapted to be connected to a different number of the plurality of wall panels to form a test cell having a plan area corresponding to the size of the roof panel.

Preferably each wall panel has a lapping plate permanently fixed to one vertical edge of the wall panel and provided with apertures for fixing with bolts to corresponding apertures provided at an adjacent vertical edge of an adjacent wall panel.

Preferably the modular test cell system is adapted for the construction of test cells according to the first aspect of the invention.

BRIEF DESCRIPTION OF THE DRAWINGS

The invention will now be described by way of example only with reference to the following drawings, in which:

FIGS. 5 to 8 are sectional views through various embodiments of the connection between adjacent wall panels of the test cell of FIG. 1.

DETAILED DESCRIPTION OF THE INVENTION

Figure 1:
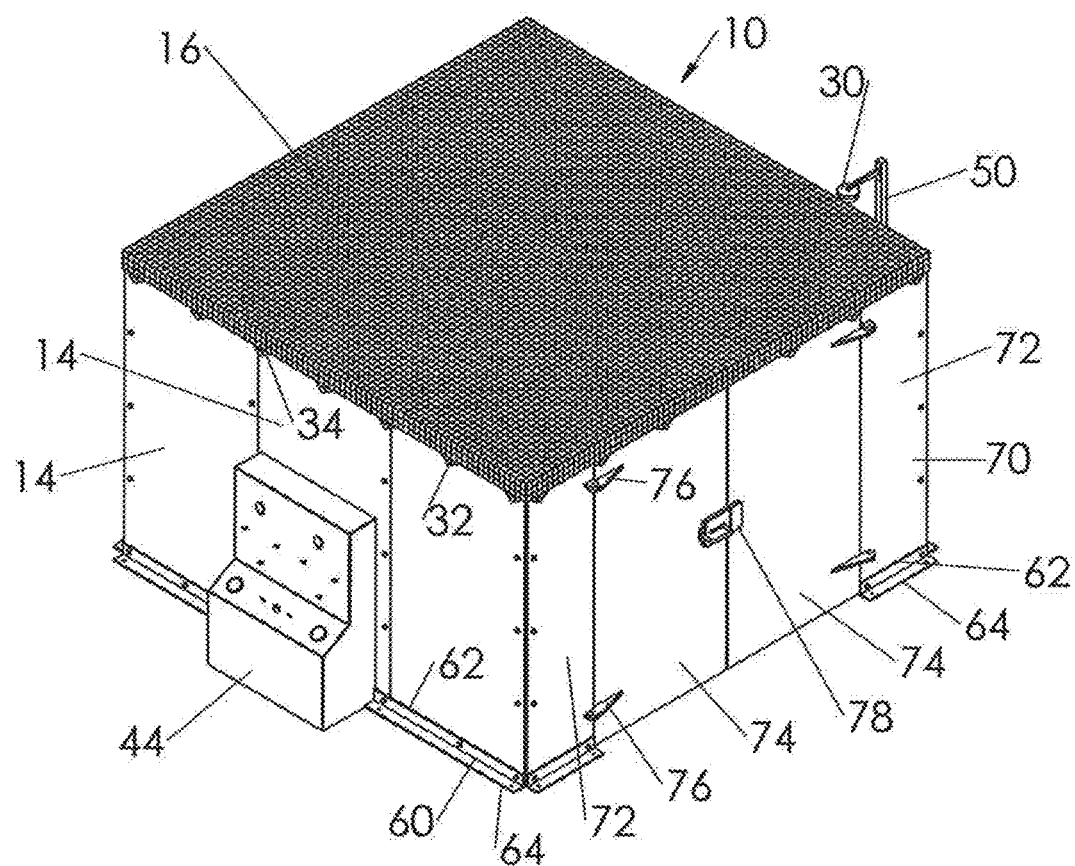
FIG. 1 shows a pressure test cell according to an embodiment of the invention.
Figure 2:
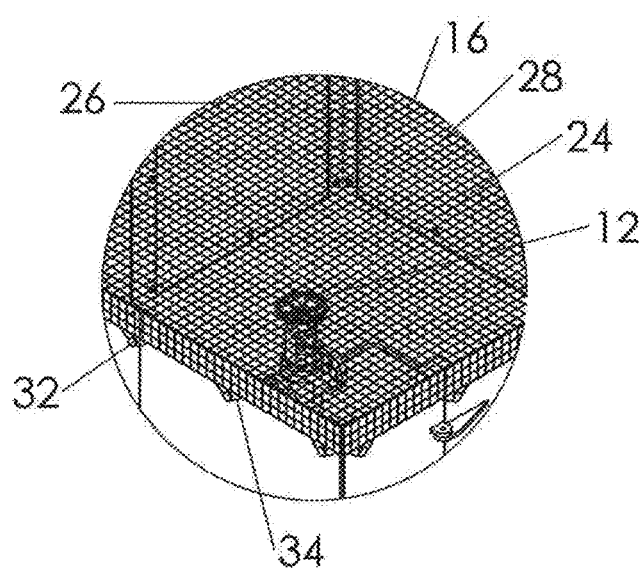
FIG. 2 is an enlarged view through the roof of the pressure test cell of FIG. 1.
Figure 3:
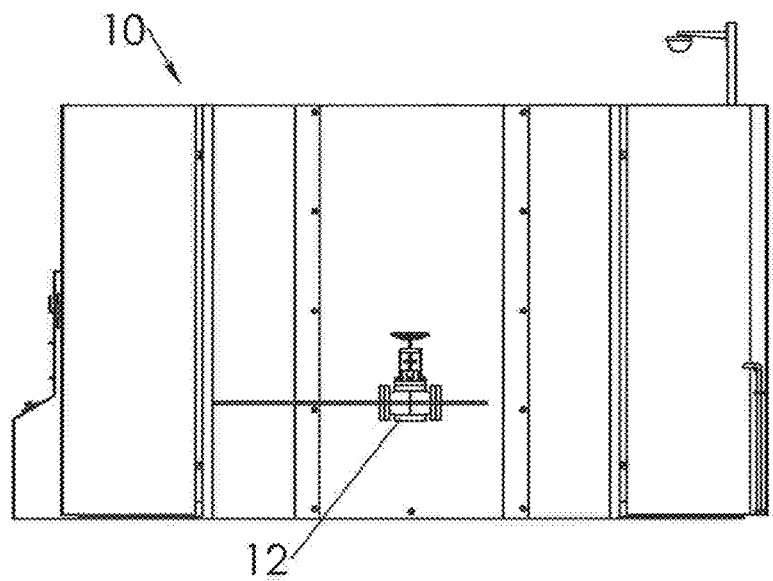
FIG. 3 shows a side view through the pressure test cell of FIG. 1 with the doors open and the roof removed.
Figure 4:
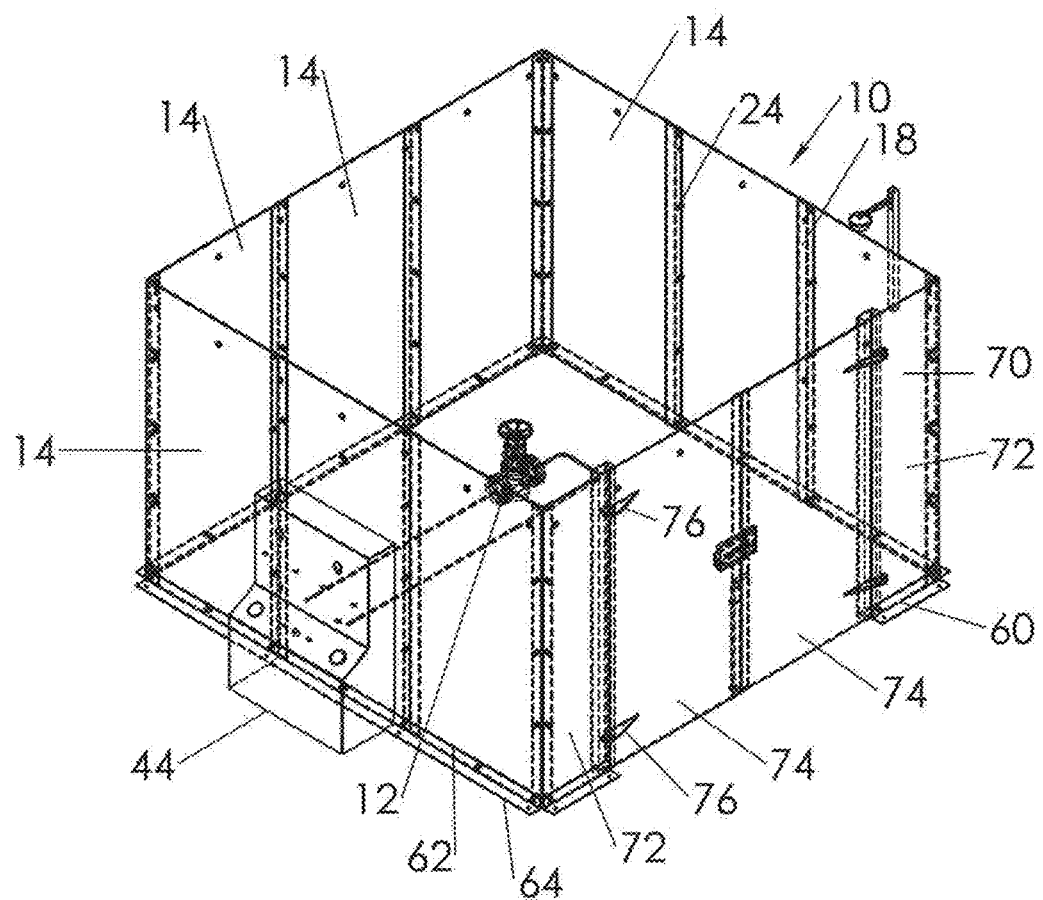
FIG. 4 is a schematic view of the pressure test cell of FIG. 1 with the roof removed showing the connection of wall panels of the test cell.

Referring to FIGS. 1 to 4, there is shown a pressure test cell 10 for containing equipment 12 subject to pressure testing. The test cell comprises a number of interconnected wall panels 14 forming an enclosure, with a roof panel 16 connected to the wall panels. Each wall panel 14 is formed from a metal plate, preferably a steel plate. The thickness of the plate is determined by the forces which it is required to contain; the forces will be dependent upon the size and mass of the equipment subject to pressure testing and the pressure at which the testing is carried out.

Each wall panel 14 is connected to an adjacent wall panel 14 by a lapped connection, comprising in this example a lapping plate 18 permanently fixed to one vertical edge of the wall panel, for example by a welded connection 20, as shown in FIG. 5. The lapping plate 18 is also of metal, preferably steel, and is provided with apertures 22 for fixing with bolts (not shown) to corresponding apertures 24 provided at an adjacent vertical edge of an adjacent wall panel 14.

The roof panel 16 comprises a mesh panel formed from mesh strands 26 of a high strength material, for example strands of wire, rope or braid of steel, metal, plastic, natural or composite fibre, or a combination thereof.

In one embodiment the mesh panel 16 may be of plastic or composite material, and may be extruded, oriented, expanded, woven or tubular. It can be made from polypropylene, polyethylene, nylon, PVC, PTFE, natural fibres, polyamides, ultra high molecular weight polyethylene (UH-MWPE) such as Dyneema™, or aramid fabrics such as Kevlar™ and Nomex™.

In another embodiment the mesh panel 16 may be of metal and may be woven, knitted, welded, expanded, photo-chemically etched or electroformed from steel or other metals.

In a preferred embodiment the mesh panel is a ballistic net of aramid fabric such as Kevlar™ and Nomex™.

The mesh panel 16 has an aperture size such that the mesh panel permits the dissipation of air pressure through the apertures 28 in the mesh panel while blocking passage through the mesh panel of fragments of the equipment 12 subject to pressure testing should the equipment fail under pressure testing and form projectile fragments. The aperture size of the mesh panel 16 is selected according to the size and mass of the equipment subject to pressure testing, the size of projectile fragments likely to be formed due to failure and the pressure at which the testing is carried out. The aperture size should be small enough to block passage through the mesh of all but the smallest fragments, while being large enough to permit observation of the equipment under test by means of a camera 30 positioned above the roof panel 16. The apertures 28 may be rectangular, hexagonal or any other appropriate shape.

Typically the mesh panel 16 has an aperture size such that the width of each aperture 28 is between 3 mm and 150 mm. In a preferred embodiment the mesh panel has an aperture size such that the width of each aperture 28 is between 12 mm and 50 mm.

Typically the mesh panel 16 blocks passage of fragments having a size of more than 25 mm. In certain circumstances a mesh panel 16 may be selected to block passage of fragments having a size of more than 12 mm. In other circumstances a mesh panel 16 may be selected to block passage of fragments having a size of more than 100 mm.

The roof panel 16 is connected to the wall panels by connecting wires or loops 30 provided around the perimeter of the roof panel 16. These connecting wires or loops 30 engage with hooks 32 which are arranged at or near the upper horizontal edge of the wall panels 14. The hooks 32 may be of any suitable shape and may be fixed to the wall panel 14 by welding or adhesive or other fixing means.

FIGS. 5 to 8 show various alternative means of connecting the wall panels 14, although the invention is not limited to any of these methods.

In the arrangement of FIG. 5 the lapping plate 18A extends in a plane parallel to the plane of the wall panel 14A and is fixed by the weld 20 to the wall panel 14A. The lapping plate 18A is fixed to an adjacent wall panel 14B coplanar with the wall panel 14A by bolts 25 which pass through apertures 22, 24 in the lapping plate 18A and adjacent wall panel 14B. The wall panels 14A and 14B thus form a continuous planar wall of the test cell 10.

In the arrangement of FIGS. 6 and 7 the lapping plate 18B is an angle member, which includes a flange portion 32 fixed to the wall panel 14C. In FIG. 6 the flange portion 32 is fixed to the wall panel 14C by bolts 25. In FIG. 7 the flange portion 32 is fixed to the wall panel 14C by the weld 20. The lapping plate 18B also includes a web portion 34 which extends perpendicular to the plane of the wall panel 14C. The web portion 34 of the lapping plate 18B is fixed to an adjacent wall panel 14D perpendicular to the wall panel 14C by bolts 25 which pass through apertures 22, 24 in the lapping plate 18B and adjacent wall panel 14D. The wall panels 14C and 14D thus form a corner of the test cell 10.

In the arrangement of FIG. 8 the lapping plate 18C extends in a plane parallel to the plane of the wall panel 14E and is fixed by the weld 20 to the wall panel 14E. The lapping plate 18C is fixed to a wall corner member 36, which in this embodiment is an angle member extending along the height of the wall panel 14E and having a flange portion 38 and a web portion 40. Other shapes may be used for the wall corner member 36, such as hollow box sections, I beams, T beams, solid bars etc. The lapping plate 18C is fixed to the flange portion 38 by bolts (not shown) which pass through apertures 22, 42 in the lapping plate 18C and flange portion 38. The adjacent wall panel 14F is fixed to the web portion 40 by bolts (not shown) which pass through apertures 24, 44 in the wall panel 14F and web portion 40. The wall panels 14E and 14F thus form a corner of the test cell 10.

The invention is not limited to any particular method of joining the wall panels 14 at the corners of the test cell 10, and any appropriate method may be used which achieves lapping of the joint.

The test cell includes testing equipment (not shown) for monitoring the equipment 12 subject to pressure testing. Any suitable testing equipment may be used, for example pressure monitoring equipment, pressurised air delivery equipment, thermal sensing equipment, or pressurised water delivery equipment. The equipment is preferably controlled from a control panel 44 on the exterior of the test cell 10. Connection hoses, pipes, electrical leads, cables and other fittings for delivering high or low pressure fluid, electrical power, high pressure gas, or control signals or similar to equipment under test can be fed through appropriate apertures (not shown) in the wall panel 14 adjacent to the control panel 44.

In order to monitor the equipment 12 subject to pressure testing during the testing process, a camera 30 is provided on a camera support structure 50 fixed to one of the wall panels 14. The camera 30 is arranged above the roof panel 16 of the test cell 10 to provide a view of the interior of the test cell 10 through the roof panel 16.

In an alternative embodiment the camera 30 may be positioned inside the test cell 10 below the roof panel 16, if the calculated failure mode of the equipment 12 under test indicates that the fragments will be smaller than the apertures 28 of the mesh panel 16. In such circumstances a substantially opaque mesh panel 16 of smaller aperture size can be used, and a camera 30 having an appropriately wide angle lens can be positioned closer to the equipment under test.

The test call can include a steel floor (not shown) or the test cell can be constructed on a concrete floor. Each wall panel is fixed to the floor by any appropriate means. In the illustrated embodiment each wall panel 14 has a floor fixing means 60 for fixing the wall panel 14 to the floor, comprising an angle member having a web 62 and a flange 64. The web 62 is fixed to the wall panel 14 by any suitable means, for example bolting or welding, and the flange member fixed to the floor by any suitable means, for example bolting or welding.

The test cell 14 may include a tank (not shown) adapted to hold liquid such as water, and a lifting means such as a hoist or crane adapted to raise and lower the equipment subject to pressure testing out of and into the tank.

One or more of the wall panels 14 may include an access door. Alternatively, as in the illustrated embodiment, the test cell 10 may include wall panels in the form of door mounting panels 70. Each door mounting panel 70 has a wall section 72, which can be connected to an adjacent wall panel in one of the ways described previously, and an access door 74 fixed by hinges 76 to the wall section 72. The doors are closed by any suitable latch, bolt or closing mechanism 78. The hinges 76 and closing mechanism 78 are selected to be strong enough to withstand pressure waves and projectiles which may arise from failure of the equipment under test. The access door or doors 74 provide a point of entry for the user to enter the test cell 10 to perform tasks before and after testing, and for bringing equipment for testing into and out of the test cell. A single door or double doors may be used.

The test cell 10 of the present invention is used to provide a method for pressure testing in an enclosed environment which is specifically designed to absorb, deflect and dissipate pressure waves created by an explosion emanating from the equipment 12 under test. The equipment 12 may be a pressure vessel, a valve or any other equipment which is designed to hold fluids under pressure. Through the pervious mesh roof 16 the test cell 10 can dissipate the pressure wave created by a build-up of quasi static pressure, as defined in the description of the background to the invention. The wall panels 14 and mesh roof 16 can entrap any fragments occurring from a failed vessel 12 within the test cell 10 with no scabbing occurring.

Although the illustrated example the test cell 10 is rectangular in plan and cuboid in shape, the test cell 10 can be of any other suitable geometric shape.

The provision of a lapping plate 18 at the edge of each wall panel 14 ensures that joints between adjacent wall panels 14 have an overlap with the adjacent wall panel 14. In the event of failure of equipment under test and the release of pressure inside the test cell 10, these lapping plates 18 transfer the pressure loading to the steel wall panels 14 and thus add to the normal force, greatly increasing the friction between the lapping plate 18 and the adjacent wall panel 14. This leads to an increase in strength of the joint between adjacent wall panels 14.

The test cell 10 described above can form part of a modular system which can be used to construct test calls 10 in a range of different sizes. Such a modular system includes a number of wall panels 14 of substantially the same size and a number of roof panels 16 of a range of different sizes. Each roof panel 16 of different size is adapted to be connected to a different number of wall panels 14 to form a test cell 10 having a plan area corresponding to the size of the roof panel 16.

For example, a first roof panel 16 has the size shown in FIG. 1, and is used to construct a test cell 10 which has a square shape in plan, each side wall of the test cell 10 having a length equivalent to three standard wall panels 14. A second roof panel (not shown) has the same width as the roof panel 16 shown in FIG. 1, and is used to construct a test cell 10 which has a rectangular shape in plan, the shorter side wall of the test cell 10 having a length equivalent to three standard wall panels 14, and the longer side wall having a length equivalent to four standard wall panels 14, so that four wall panels 14 are connected together to form the longer side walls.

As will be understood, the modular nature of the system means that any number of wall panels 14 may be chosen to form a side wall of the test cell 10.

This method of using a modular system and standardised sizes allows for more rapid construction and assembly of the test cell 10, with each panel being constructed in a similar fashion. It also facilitates rapid modification of a test cell 10, in cases where an increase or decrease in test cell size is required.

The thickness of the wall panels 14, doors 74 and door bolt 78 can vary from that shown in the drawings, dependent on the pressure to be contained as a result of failure of the specific equipment 12 under test. An appropriate calculation is made taking into account the likely failure modes of the equipment 12 under test. For example, when testing a valve, the pressure, the size of the stored pressurised volume, the medium under pressure (for example air or water) and likely failure modes define the likely size and velocity of fragments arising from rupture or failure of the valve. Typically the failure modes considered for valves are: failure due to brittle fracture, failure of an end connection, rocketing of the valve, and ejection of small and large fragments.

The test cell 10 is secured to the floor or ground by bolts and steel L sections or angle members 60 of a size and material specifically calculated in strength so as to prevent the test cell 10 from warping and freeing itself from the ground when pressure is released due to failure of the equipment 12 under test. In the event of damage occurring at the joints between adjacent wall panels 14 due to the released pressure, the L section of the angle members 60 provides rotational stiffness at ground level to reduce the chance of the wall panels 14 becoming loose and being pushed over by the pressure wave.

The closure mechanism 78 shown in FIG. 1 includes a sliding bolt and housing that the bolt slides into. The cross-sectional size of the bolt is chosen according to the requirements of the particular test cell 10 and is calculated in a similar way to the way in which the thickness of the wall panels 14 is calculated. This ensures that the closure mechanism 78 can withstand the forces applied to it when a pressure wave or fragment comes into contact with the doors 74 to which it is attached, thereby preventing failure of the doors themselves. Additional stiffness is provided in the region of the hinges by the use of steel channel sections 80 welded to the door mounting panels 70 and/or doors 74. This reduces any point loading distortion in the vicinity of the attachment point of the hinges 76.

The roof panel 16 is constructed out of a material which is specifically created for this structure. The roof panel must be sufficiently porous to allow venting of a pressure pulse generated by failure of the equipment under test. It must therefore have open areas. To allow sufficient venting typically at least 25% of the area of the roof panel 16 comprises voids. In other words apertures make up at least 25% of the area of the roof panel, the remaining area being made up of the strands of the mesh panel. In a preferred embodiment at least 50% of the area of the roof panel 16 comprises voids. The size of the mesh aperture 24 and the size and strength of the strands 28 are calculated taking into consideration to likely failure modes of the equipment 12 under test, based on a relationship between pressure and failure modes which defines the likely size and velocity of fragments that would emanate from the equipment 12 under test. In this way a mesh panel can be designed to catch any of these fragments.

The higher the test pressure and the larger the pressurised volume of the equipment under test, the larger the stored energy that will be released in the event of a failure of the equipment. This means that the mesh panel will need to slow down and stop items with large amounts of kinetic energy. This is a driver towards using thicker material and thicker strands in the mesh panel.

The aperture size determines the minimum size of fragment that can be captured. This is a driver towards providing smaller apertures in the mesh panel. Thus according to the invention a balance is achieved, based on the likely fragment size and energy of the fragments on one hand, and the need to vent pressure and to allow a camera to monitor the testing through the mesh panel on the other hand.

Higher energy failures are likely to produce significantly larger fragments. The smallest fragment in testing of large valves is likely to be a pressure connector with an approximate diameter of 25 mm. Typically the test is carried out so that under the most likely failure mode fragments are driven horizontally. For this reason netting sizes would typically start with 25 mm aperture size. Where the pressure testing is anticipated to use higher pressures and larger items of equipment leading to larger fragments, so there is a need for stronger netting to slow down and stop the fragments, a larger aperture size of up to 100 to 150 mm may be used, together with larger fibres or groups of fibres used as the strands of the mesh.

The scope of the claims is not limited to the particular embodiments described herein. Other embodiments and variations are possible, in particular other methods of connecting wall panels 14 and of joining the roof panel 16 to the wall panels, other methods of fixing the wall panels 14 to the floor or ground, and other forms of access to the interior of the test cell 10.

The invention claimed is:

1. A test cell for containing equipment subject to testing, the test cell comprising:
   a plurality of wall panels, each wall panel comprising a lapped connection with an adjacent wall panel;
   a roof panel fixedly connected to the plurality of wall panels;
   wherein each wall panel comprises a metal plate;
   wherein the roof panel comprises a mesh panel for entrapping fragments of equipment in the event of an explosion emanating from the equipment; and wherein the equipment comprises at least one of pressure monitoring equipment, pressurised air delivery equipment, thermal sensing equipment, and pressurised water delivery equipment.

2. The test cell according to claim 1, wherein each lapped connection comprises a lapping plate fixed to one vertical edge of a corresponding wall panel and provided with apertures for fixing with bolts to corresponding apertures provided at an adjacent vertical edge of an adjacent wall panel.

3. The test cell according to claim 1, wherein the mesh panel is a ballistic net.

4. The test cell according to claim 1, wherein the mesh panel has apertures having an aperture size such that the width of each aperture is at least 5 mm.

5. The test cell according to claim 1, wherein the roof panel is connected to the plurality of wall panels by a plurality of hooks arranged at an upper horizontal edge of each of the plurality of wall panels.

6. The test cell according to claim 1, wherein strands of the mesh panel comprise at least one of wire, rope and braid of steel, metal, plastic, natural fibre, and composite fibre.

7. The test cell according to claim 1, wherein:
the mesh panel comprises apertures between mesh strands; and
the apertures make up at least 25% of the area of the mesh panel.

8. The test cell according to claim 1, comprising a camera fixed to one of said wall panels and arranged above the roof panel of the test cell to provide a view of the interior of the test cell through the roof panel.

9. The test cell according to claim 1, comprising:
a floor; and
wherein each wall panel is fixed to the floor.

10. The test cell according to claim 9, wherein the floor is a steel floor.

11. The test cell according to claim 9, comprising:
a tank adapted to hold liquid; and
lifting means adapted to lower the equipment subject to pressure testing into the tank and to raise the equipment subject to pressure testing from the tank.

12. The test cell according to claim 11, wherein the tank comprises a pit in the floor.

13. The test cell according to claim 1, comprising a plurality of wall corner members, each wall corner member being adapted for connection with at least one of said wall panels.

14. The test cell according to claim 1, wherein one of said wall panels includes a door.

15. The test cell according to claim 14, wherein at least one of said wall panels comprises a door mounting panel comprising a wall section and a door hingedly fixed to the wall section.

16. A test cell system for construction of test cells for containing equipment subject to testing, the test cell system comprising:
a plurality of wall panels adapted for connection to other wall panels to form walls of a test cell, each of said wall panels having the same size;
a plurality of roof panels adapted for connection to said plurality of wall panels, each of said roof panels having a different size;
wherein each wall panel comprises a metal plate;
wherein each roof panel comprises a mesh panel for entrapping fragments of the equipment in the event of an explosion emanating from the equipment;
wherein the size of each roof panel is adapted such that it can be connected to a different number of wall panels, which are connected to four wall corner members, to form a test cell of a corresponding size; and
wherein the equipment comprises at least one of pressure monitoring equipment, pressurised air delivery equipment, thermal sensing equipment, and pressurised water delivery equipment.

17. The test cell system according to claim 16, wherein each wall panel has a lapping plate permanently fixed to one vertical edge of the wall panel and provided with apertures for fixing with bolts to corresponding apertures provided at an adjacent vertical edge of an adjacent wall panel.

18. The test cell system according to claim 16, wherein each test cell comprises:
a plurality of wall panels, each wall panel comprising a lapped connection with an adjacent wall panel;
a roof panel fixedly connected to the plurality of wall panels;
wherein each wall panel comprises a metal plate; and
wherein the roof panel comprises a mesh panel for entrapping fragments of equipment in the event of an explosion emanating from the equipment subject to testing.

\* \* \* \* \*